(12) United States Patent
Gellman et al.

(10) Patent No.: US 6,997,926 B2
(45) Date of Patent: Feb. 14, 2006

(54) RESISTANCE HEATED TISSUE MORCELLATION

(75) Inventors: Barry N. Gellman, North Easton, MA (US); Josef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 453 days.

(21) Appl. No.: 10/067,488

(22) Filed: Feb. 4, 2002

(65) Prior Publication Data

US 2003/0149442 A1   Aug. 7, 2003

(51) Int. Cl.
*A61B 17/39* (2006.01)

(52) U.S. Cl. ........................................ 606/46; 606/170
(58) Field of Classification Search .......... 606/41–46, 606/47–50, 170–181
See application file for complete search history.

(56) References Cited

U.S. PATENT DOCUMENTS

| | | | |
|---|---|---|---|
| 1,586,645 A | 6/1926 | Bieman | |
| 1,814,791 A | 7/1931 | Ende | |
| 1,930,214 A | 10/1933 | Wappler | |
| 1,963,636 A | 6/1934 | Wappler | |
| 1,971,024 A | 8/1934 | Wappler | |
| 2,002,594 A | 5/1935 | Wappler et al. | |
| 2,004,559 A | 6/1935 | Wappler et al. | |
| 2,011,169 A | 8/1935 | Wappler | |
| 2,056,377 A | 10/1936 | Wappler | |
| 2,090,923 A | 8/1937 | Wappler | |
| 2,101,913 A | 12/1937 | Meyer | |
| 2,224,464 A | 12/1940 | Wolf | |
| 2,484,059 A | 10/1949 | Wallace | |
| 2,487,502 A | 11/1949 | Willinsky | |
| 2,815,757 A | 12/1957 | Piar | |
| 2,955,591 A | 10/1960 | MacLean | |
| 3,149,633 A | 9/1964 | Zingale | |
| 3,752,159 A | 8/1973 | Wappler | |
| 3,856,015 A | 12/1974 | Iglesias | |
| 3,910,279 A | 10/1975 | Okada et al. | |
| 3,939,839 A | 2/1976 | Curtiss | |
| 3,973,568 A | 8/1976 | Iglesias | |
| 3,982,542 A | 9/1976 | Ford et al. | |
| 3,985,137 A | 10/1976 | Donohue | |
| 3,990,456 A | 11/1976 | Iglesias | |
| 4,030,502 A | 6/1977 | Iglesias | |
| 4,051,855 A | 10/1977 | Schneiderman | |
| 4,060,087 A | 11/1977 | Hiltebrandt et al. | |
| 4,061,146 A | 12/1977 | Baehr et al. ................ 128/305 |

(Continued)

FOREIGN PATENT DOCUMENTS

DE        2514501        10/1976

(Continued)

OTHER PUBLICATIONS

American ACMI, "ACMI Adult Resectoscopes Operating & Maintenance Manual", Jun. 1984, 3 pages.

(Continued)

*Primary Examiner*—Vy Bui
(74) *Attorney, Agent, or Firm*—Edwards Angell Palmer & Dodge LLP

(57) ABSTRACT

A morcellator is designed to comminute tissue. The morcellator includes a rotatable electrode and a drive system. The rotatable electrode has a resistance to the flow of an electrical current. The electrode is heated by the flow of the current through the rotatable electrode. The rotatable electrode is also rotated by the drive system as the rotatable electrode is heated by the flow of the current. The rotation and heating of the rotatable electrode enables the morcellator to comminute tissue.

14 Claims, 14 Drawing Sheets

U.S. PATENT DOCUMENTS

| | | | |
|---|---|---|---|
| 4,089,336 A | 5/1978 | Cage et al. | 128/303.1 |
| 4,103,688 A | 8/1978 | Edwards | |
| 4,116,198 A | 9/1978 | Roos | |
| 4,134,406 A | 1/1979 | Iglesias | |
| 4,149,538 A | 4/1979 | Mrava et al. | |
| 4,190,051 A | 2/1980 | Iglesias | |
| 4,196,734 A | 4/1980 | Harris | 128/303.1 |
| 4,333,467 A | 6/1982 | Domicone | |
| 4,347,849 A | 9/1982 | Congdon | |
| 4,362,160 A | 12/1982 | Hiltebrandt | |
| 4,506,668 A | 3/1985 | Konig | |
| 4,538,610 A | 9/1985 | Kubota | |
| 4,560,373 A | 12/1985 | Sugino et al. | |
| 4,648,399 A | 3/1987 | Nakada | |
| 4,649,917 A | 3/1987 | Karasawa | |
| 4,657,018 A | 4/1987 | Hakky | |
| 4,674,499 A | 6/1987 | Pao | |
| 4,709,698 A | 12/1987 | Johnston et al. | |
| 4,726,370 A | 2/1988 | Karasawa et al. | |
| 4,815,462 A | 3/1989 | Clark | 128/305 |
| 4,832,048 A | 5/1989 | Cohen | 128/786 |
| 4,848,346 A | 7/1989 | Crawford | |
| 4,862,890 A | 9/1989 | Stasz et al. | |
| 4,899,741 A | 2/1990 | Bentley et al. | |
| 4,917,082 A | 4/1990 | Grossi et al. | |
| 4,919,131 A | 4/1990 | Grossi et al. | |
| 4,934,367 A | 6/1990 | Daglow et al. | |
| 4,936,301 A | 6/1990 | Rexroth et al. | |
| 4,946,440 A | 8/1990 | Hall | |
| 4,955,882 A | 9/1990 | Hakky | |
| 4,976,711 A | 12/1990 | Parins et al. | |
| 4,994,062 A | 2/1991 | Nishigaki et al. | |
| 5,007,907 A | 4/1991 | Nishigaki et al. | |
| 5,007,908 A | 4/1991 | Rydell | |
| 5,013,312 A | 5/1991 | Parins et al. | |
| 5,019,076 A | 5/1991 | Yamanashi et al. | |
| 5,029,573 A | 7/1991 | Chow | |
| 5,030,090 A | 7/1991 | Maeda et al. | |
| 5,041,111 A | 8/1991 | Bauer et al. | |
| 5,045,061 A | 9/1991 | Seifert et al. | |
| 5,047,027 A | 9/1991 | Rydell | |
| D320,446 S | 10/1991 | Grossi et al. | |
| 5,056,529 A | 10/1991 | de Groot | |
| 5,057,105 A | 10/1991 | Malone et al. | 606/28 |
| 5,059,200 A | 10/1991 | Tulip | |
| 5,061,266 A | 10/1991 | Hakky | |
| 5,064,424 A | 11/1991 | Bitrolf | |
| 5,074,862 A | 12/1991 | Rausis | |
| 5,078,717 A | 1/1992 | Parins et al. | |
| 5,080,660 A | 1/1992 | Buelna | |
| 5,085,658 A | 2/1992 | Meyer | |
| 5,088,998 A | 2/1992 | Sakashita et al. | |
| 5,098,431 A | 3/1992 | Rydell | |
| 5,100,402 A | 3/1992 | Fan | |
| 5,116,615 A | 5/1992 | Gokcen et al. | |
| 5,122,138 A | 6/1992 | Manwaring | |
| 5,125,928 A | 6/1992 | Parins et al. | |
| 5,171,311 A | 12/1992 | Rydell et al. | |
| 5,176,677 A | 1/1993 | Wuchinich | |
| 5,192,280 A | 3/1993 | Parins | |
| 5,196,011 A | 3/1993 | Korth et al. | |
| 5,197,964 A | 3/1993 | Parins | |
| 5,201,731 A | 4/1993 | Hakky | |
| 5,201,741 A | 4/1993 | Dulebohn | |
| 5,207,672 A | 5/1993 | Roth et al. | |
| 5,213,097 A | 5/1993 | Zeindler | 128/401 |
| 5,252,090 A | 10/1993 | Giurtino et al. | |
| 5,258,006 A | 11/1993 | Rydell et al. | |
| 5,269,780 A | 12/1993 | Roos | |
| 5,277,696 A | 1/1994 | Hagen | |
| 5,290,286 A | 3/1994 | Parins | |
| 5,306,287 A | 4/1994 | Becker | 606/205 |
| 5,318,564 A | 6/1994 | Eggers | |
| 5,324,288 A | 6/1994 | Billings et al. | |
| 5,330,470 A | 7/1994 | Hagen | |
| 5,341,816 A | 8/1994 | Allen | |
| 5,342,357 A | 8/1994 | Nardella | |
| 5,354,295 A | 10/1994 | Guglielmi et al. | |
| 5,354,296 A | 10/1994 | Turkel | |
| 5,366,443 A | 11/1994 | Eggers et al. | |
| 5,374,188 A | 12/1994 | Frank et al. | |
| 5,376,087 A | 12/1994 | Haber et al. | |
| 5,380,320 A | 1/1995 | Morris | |
| 5,395,312 A | 3/1995 | Desai | |
| 5,395,363 A | 3/1995 | Billings et al. | |
| 5,395,368 A | 3/1995 | Ellman et al. | |
| 5,396,900 A | 3/1995 | Slater et al. | |
| 5,397,320 A | 3/1995 | Essig et al. | |
| 5,397,342 A | 3/1995 | Heil, Jr. et al. | |
| 5,403,311 A | 4/1995 | Abele et al. | |
| 5,405,373 A | 4/1995 | Petersson et al. | |
| 5,423,812 A | 6/1995 | Ellman et al. | |
| 5,423,813 A | 6/1995 | Kaiser et al. | |
| 5,427,115 A | 6/1995 | Rowland et al. | |
| 5,439,474 A | 8/1995 | Li | 606/184 |
| 5,443,472 A | 8/1995 | Li | 606/114 |
| 5,445,635 A | 8/1995 | Denen et al. | 606/27 |
| 5,451,224 A | 9/1995 | Goble et al. | 606/48 |
| 5,454,807 A | 10/1995 | Lennox et al. | |
| 5,478,350 A | 12/1995 | Kratsch et al. | |
| 5,480,417 A | 1/1996 | Hascoet et al. | 607/101 |
| 5,482,037 A | 1/1996 | Borghi | |
| 5,484,435 A | 1/1996 | Fleenor et al. | |
| 5,506,038 A | 4/1996 | Knapp et al. | |
| 5,508,368 A | 4/1996 | Knapp et al. | |
| 5,509,929 A | 4/1996 | Hascoet et al. | 607/101 |
| 5,514,130 A | 5/1996 | Baker | |
| 5,527,331 A * | 6/1996 | Kresch et al. | 606/170 |
| 5,540,685 A | 7/1996 | Parins et al. | |
| 5,549,605 A | 8/1996 | Hahnen | |
| 5,569,244 A | 10/1996 | Hahnen | |
| 5,569,284 A | 10/1996 | Young et al. | 606/180 |
| 5,574,130 A | 11/1996 | Haeussling et al. | |
| 5,593,406 A | 1/1997 | Eggers et al. | |
| 5,603,711 A | 2/1997 | Parins et al. | |
| 5,611,803 A | 3/1997 | Heaven et al. | 606/114 |
| 5,618,296 A | 4/1997 | Sorensen et al. | 606/180 |
| 5,658,280 A | 8/1997 | Issa | |
| 5,669,876 A | 9/1997 | Schechter et al. | 604/50 |
| 5,669,927 A | 9/1997 | Boebel et al. | 606/180 |
| D385,351 S | 10/1997 | Manzie et al. | |
| 5,681,282 A | 10/1997 | Eggers et al. | |
| 5,683,366 A | 11/1997 | Eggers et al. | |
| 5,683,443 A | 11/1997 | Munshi et al. | |
| 5,685,840 A | 11/1997 | Schechter et al. | 604/22 |
| 5,693,052 A | 12/1997 | Weaver | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,697,926 A | 12/1997 | Weaver | |
| 5,709,680 A | 1/1998 | Yates et al. | |
| 5,718,709 A | 2/1998 | Considine et al. | |
| 5,720,745 A | 2/1998 | Farin et al. | |
| 5,730,752 A | 3/1998 | Alden et al. | 606/180 |
| 5,746,746 A | 5/1998 | Garito et al. | |
| 5,749,870 A | 5/1998 | Gloth et al. | |
| 5,755,717 A | 5/1998 | Yates et al. | |
| 5,766,168 A | 6/1998 | Mantell | |
| 5,766,170 A | 6/1998 | Eggers | |
| 5,766,171 A | 6/1998 | Silvestrini | |
| 5,776,128 A | 7/1998 | Eggers | |
| 5,779,701 A | 7/1998 | McBrayer et al. | |
| H1745 H | 8/1998 | Paraschac | |

| | | | |
|---|---|---|---|
| 5,807,394 A | 9/1998 | Sakai et al. ............ 606/39 |
| 5,810,764 A | 9/1998 | Eggers et al. .......... 604/23 |
| 5,810,808 A | 9/1998 | Eggers |
| 5,810,811 A | 9/1998 | Yates et al. |
| 5,827,274 A | 10/1998 | Bonnet et al. |
| 5,830,214 A | 11/1998 | Flom et al. |
| 5,833,689 A | 11/1998 | Long |
| 5,837,003 A | 11/1998 | Ginsburg ............... 607/106 |
| 5,843,019 A | 12/1998 | Eggers et al. |
| 5,846,241 A | 12/1998 | Kittur et al. |
| 5,860,976 A | 1/1999 | Billings et al. |
| 5,871,469 A | 2/1999 | Eggers et al. |
| 5,888,198 A | 3/1999 | Eggers et al. |
| 5,906,615 A | 5/1999 | Thompson ............... 606/45 |
| 5,919,191 A | 7/1999 | Lennox et al. ......... 606/48 |
| 5,935,125 A | 8/1999 | Zupkas |
| 6,023,638 A | 2/2000 | Swanson ............... 600/510 |
| 6,032,673 A | 3/2000 | Savage et al. ......... 128/898 |
| 6,033,400 A | 3/2000 | Grossi et al. |
| 6,039,748 A | 3/2000 | Savage et al. ......... 606/180 |
| 6,047,218 A | 4/2000 | Whayne et al. ........ 607/122 |
| 6,066,153 A | 5/2000 | Lev ....................... 606/180 |
| 6,113,594 A | 9/2000 | Savage ................... 606/41 |
| 6,152,919 A | 11/2000 | Hakky .................... 606/15 |
| 6,152,932 A | 11/2000 | Ternstrom ............. 606/114 |
| 6,156,049 A | 12/2000 | Lovato et al. ......... 606/170 |
| 6,162,235 A | 12/2000 | Vaitekunas ............ 606/169 |
| 6,212,426 B1 | 4/2001 | Swanson ............... 600/510 |
| 6,251,108 B1 | 6/2001 | Irion et al. |
| 6,296,639 B1 * | 10/2001 | Truckai et al. .......... 606/41 |

FOREIGN PATENT DOCUMENTS

| | | |
|---|---|---|
| DE | 37 07 403 A1 | 9/1987 |
| DE | 37 07 820 C2 | 9/1987 |
| DE | 37 07 821 A1 | 9/1988 |
| EP | 0 544 392 A1 | 6/1993 |
| FR | 2594322 | 2/1986 |
| GB | 2213381 A | 8/1989 |
| SU | 1311726 | 5/1987 |
| WO | WO 93/13719 | 7/1993 |
| WO | WO 93/21845 | 11/1993 |
| WO | WO 95/10981 | 4/1995 |
| WO | WO 96/11638 | 4/1996 |
| WO | WO 96/23449 | 8/1996 |
| WO | WO 97/15238 | 5/1997 |
| WO | WO 97/17027 | 5/1997 |
| WO | WO 97/17028 | 5/1997 |
| WO | WO 97/24993 | 7/1997 |
| WO | WO 97/49346 | 12/1997 |

OTHER PUBLICATIONS

Crispin, H. and Verhulst, A.; "Use of the Vascular Brush in Angioscopically-Assisted Endarterectomy", Journal of Interventional Cardiology; vol. 7, No. 1, Feb. 1994, p. 92.

DLC-14: Diamonex® Product Brochure, by Diamonex® Performance Products, A Unit of Monsanto Company, 33 pages; 1997.

http://members.aol.com/getscc, Oct. 26, 1998, 6 pages.

International Search Report for PCT/US98/20112, Feb. 8, 1999; 9 pages.

Product Literature for WEDGE™; Microvasive, Boston Scientific Corporation, 2 pages.

Products for Electrosurgery Product Brochure, by Microvasive, Boston Scientific Corporation, 1996, 2 pages.

The Gray Sheet, "Arthocare Urological, Gynecological Electrosurgery Systems Under Review by FDA, Firm says in IPO Filing; Launch of Core Arthrosopic Systems Begins", FDC Acc. No. 01220040006, vol. 22, Iss. 4, Jan. 22, 1996.

ACMI, USA Elite System™ & USA Series™ Grooved VaporTome® VaporElectrode, color coded black, Catalog No.: VE-LG, http://www.acmicorp.com/acmi/user/display.cfm?display=product&pid=817& catid=0, web page accessed on Jan. 22, 2004, 2 pages.

ACMI, USA Elite System™ & USA Series™ Resectoscope Electrodes, http://www.acmicorp.com/acmi/user/display.cfm?display=product&pid=2062&catid=0, web page accessed on Jan. 22, 2004, 2 pages.

Patent Cooperation Treaty, International Search Report, International Application No. PCT/US03/00735, mailed on May 15, 2003, 7 pages.

US 5,688,268, 11/1997, Billings (withdrawn)

* cited by examiner

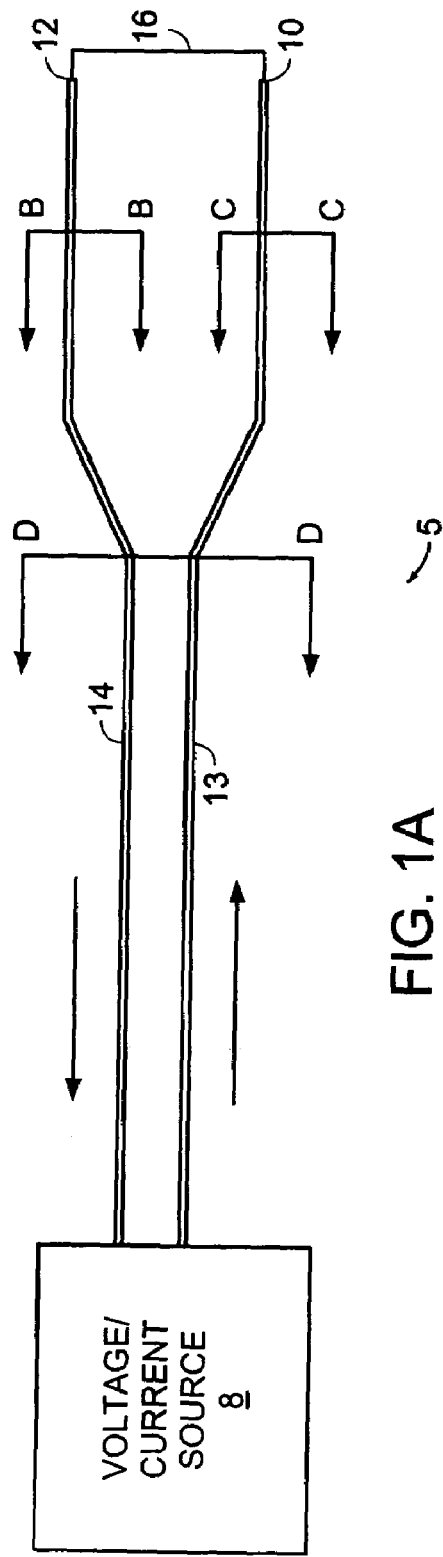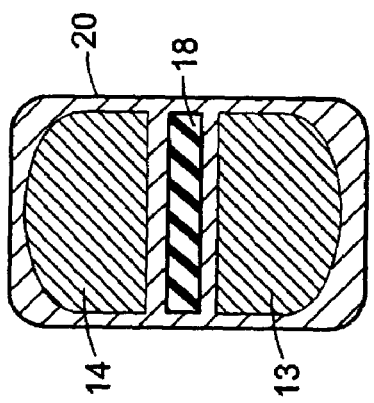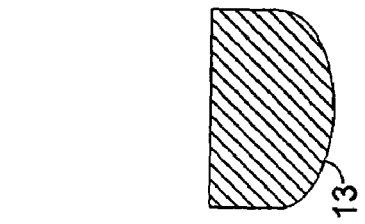

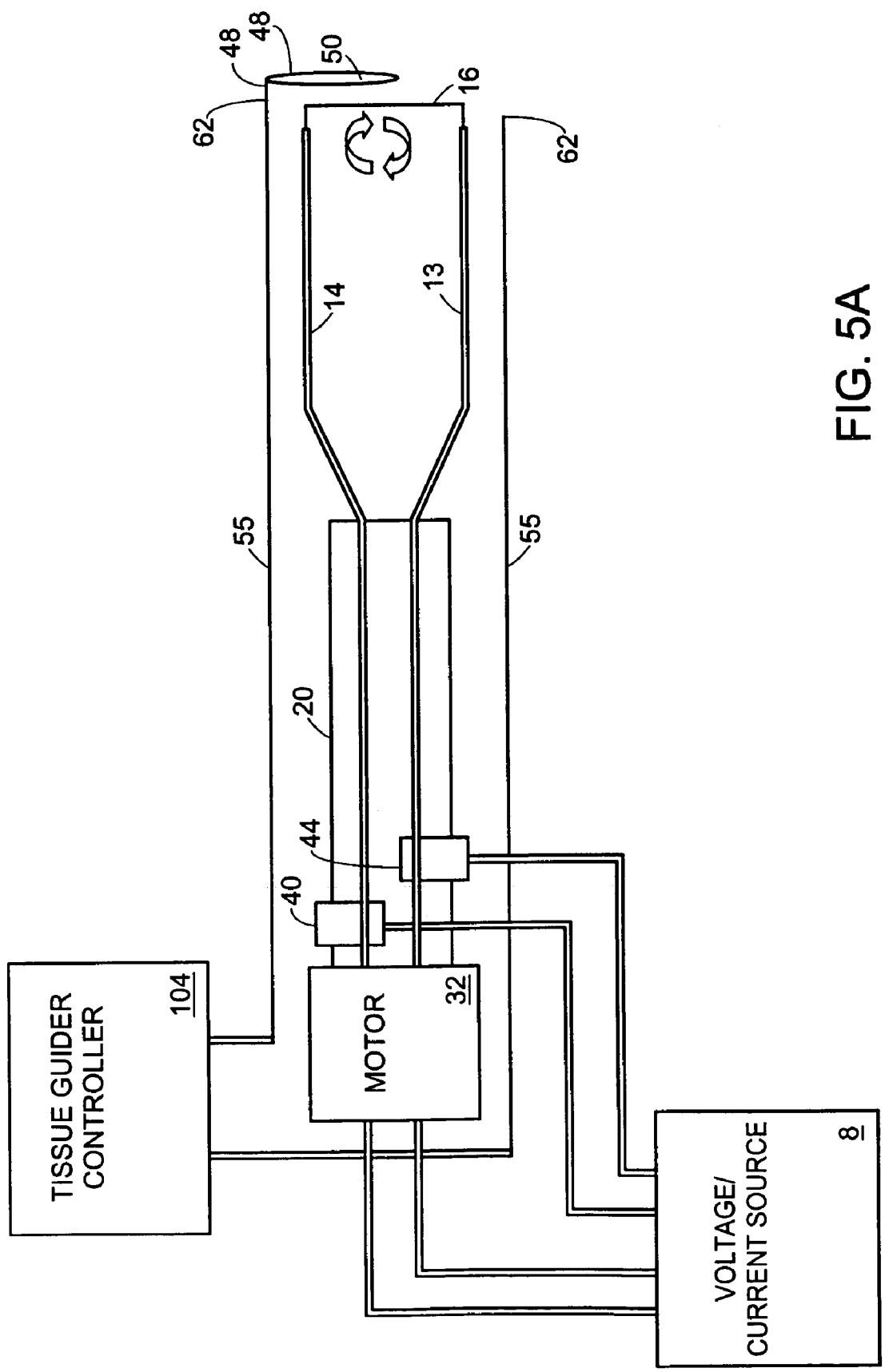

RESISTANCE HEATED TISSUE MORCELLATION

TECHNICAL FIELD

This invention generally relates to morcellating tissue and, more specifically, using a rotating resistance heated (RH) electrode to morcellate the tissue.

BACKGROUND INFORMATION

The male urethra is generally a tubular passageway extending from the bladder to the end of the penis. As urine travels from the bladder and out of the body, the urine passes through four sections of the urethra, referred to as the prostatic urethra, the membranous urethra, the bulbar urethra, and the pendulous or distal urethra. Surrounding the prostatic urethra and below the bladder is a prostate gland, which, among other functions, produces the fluid in semen.

A urological condition that some, mostly male, patients experience is blockage of the urethra. For instance, prostate enlargement, also known as benign prostate hyperplasia (BPH), is a common affliction experienced by some men. The condition involves swelling of the prostate, which prevents passage of urine from the bladder and consequently makes urination difficult or impossible. Prostate cancer is another affliction suffered by some men and may lead to many of the same symptoms as BPH.

BPH is often treated by surgically removing the excess prostatic tissue from the interior region of the prostate that is pressing on the urethra. This removal usually relieves the obstruction and the incomplete emptying of the bladder caused by the BPH, leaving the rest of the prostatic tissue intact.

During a transurethral resection of the prostate gland (TURP) procedure, a surgeon uses an electrosurgical cutting loop to remove the obstructing tissue from the prostate. The electrosurgical cutting loop typically uses radio frequency (RF) electricity to "shave" off small pieces of the targeted prostate tissue from the interior of the prostate. The pieces of prostatic tissue excised by the RF electrosurgical loop are typically small enough to rapidly flush out using irrigation fluid, aspirated out using, for example, a large bore syringe, or grasped and removed.

The holmium laser resection of the prostate (HOLRP) procedure uses laser light from a holmium laser system to remove the targeted prostatic tissue. The laser light cuts the excess tissue from the interior of the prostate while coagulating the underlying tissue. The holmium laser may reduce the time period needed to resect the necessary tissue off of the prostate because the laser resects large pieces of tissue from the enlarged prostate at one time.

SUMMARY OF THE INVENTION

The rapid removal of resected tissue segments from the patient's body when employing an electrosurgical cutting loop for the TURP procedure is offset by the time required to complete the resection procedure due to the small size of the resected pieces of tissue. The resection can be completed sooner using the HOLRP procedure, but the large pieces of tissue resected by the holmium laser then require extra time to be broken down, which adds to the total time of the procedure. The large resected pieces need to be broken down until they are adequately sized for removal from the body. The invention involves a device that can be used to comminute, or reduce the size of, an object (e.g., tissue). The device can then transport the small pieces to another location, such as out of a patient's body. A morcellator according to the invention has a rotatable, resistance heated (RH) electrode. The morcellator can be used to efficiently and quickly morcellate or comminute relatively large pieces of tissue. Such a morcellator can be used in a HOLRP procedure to reduce the total time of the procedure.

In one aspect, the invention generally relates to a morcellator that includes a rotatable electrode and a drive system for rotating the rotatable electrode. The rotatable electrode has a resistance to a flow of an electrical current. The rotatable electrode is heated by the flow of the current through the rotatable electrode while the drive system rotates the rotatable electrode.

Embodiments of this aspect of the invention can include the following features. The morcellator can include a source of electrical current that is couplable to the rotatable electrode. The source can supply electrical current to the electrode so that the electrode is maintained at a temperature sufficient to comminute tissue. The morcellator may also include an outer sheath containing at least some of the rotatable electrode. The morcellator can have a vacuum source couplable to the outer sheath to provide suction, which can be used to remove comminuted tissue. In a further embodiment, the morcellator includes a tissue guider that is moveable with respect to the outer sheath to direct tissue to the rotatable electrode. The proximal end of the tissue guider may include a loop. The morcellator may also include a tissue guider controller to enable the guider to direct the tissue to the rotatable electrode at a controlled rate.

In another aspect, the invention includes a method of morcellating tissue in the body of a patient. The method includes heating a rotatable electrode having a resistance to the flow of an electrical current. The heating of the rotatable electrode is due to the flow of the current through the rotatable electrode. The rotatable electrode is also rotated as the electrode is being heated to comminute tissue. In one embodiment, the method also includes directing the tissue to the rotatable electrode to comminute tissue. The method may also include removing comminuted tissue, such as with irrigation fluid. Other embodiments include directing the tissue into the rotatable electrode and providing information about a voltage drop across and the flow of the current through the rotatable electrode.

The directional terms proximal and distal require a point of reference. In this document, the point of reference in determining direction is in the perspective of the patient. The term "proximal" refers to a direction that points into the patient's body, and the term "distal" refers to a direction that points out of the patient's body.

The foregoing and other objects, aspects, features, and advantages of the invention will become more apparent from the following description and from the claims.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention.

FIG. 1A shows a schematic view of a morcellator including a resistance heated (RH) electrode.

FIG. 1B is a cross sectional view of an electrode lead of the morcellator of FIG. 1A, taken along line BB of FIG. 1A.

FIG. 1C is a cross sectional view of another electrode lead of the morcellator of FIG. 1A, taken along line CC of FIG. 1A.

FIG. 1D is a cross sectional view of the morcellator of FIG. 1A, taken along line DD of FIG. 1A.

FIG. 5A illustrates a schematic view of the morcellator of FIG. 3A, including a tissue guider controller.

DESCRIPTION

Figure 2:
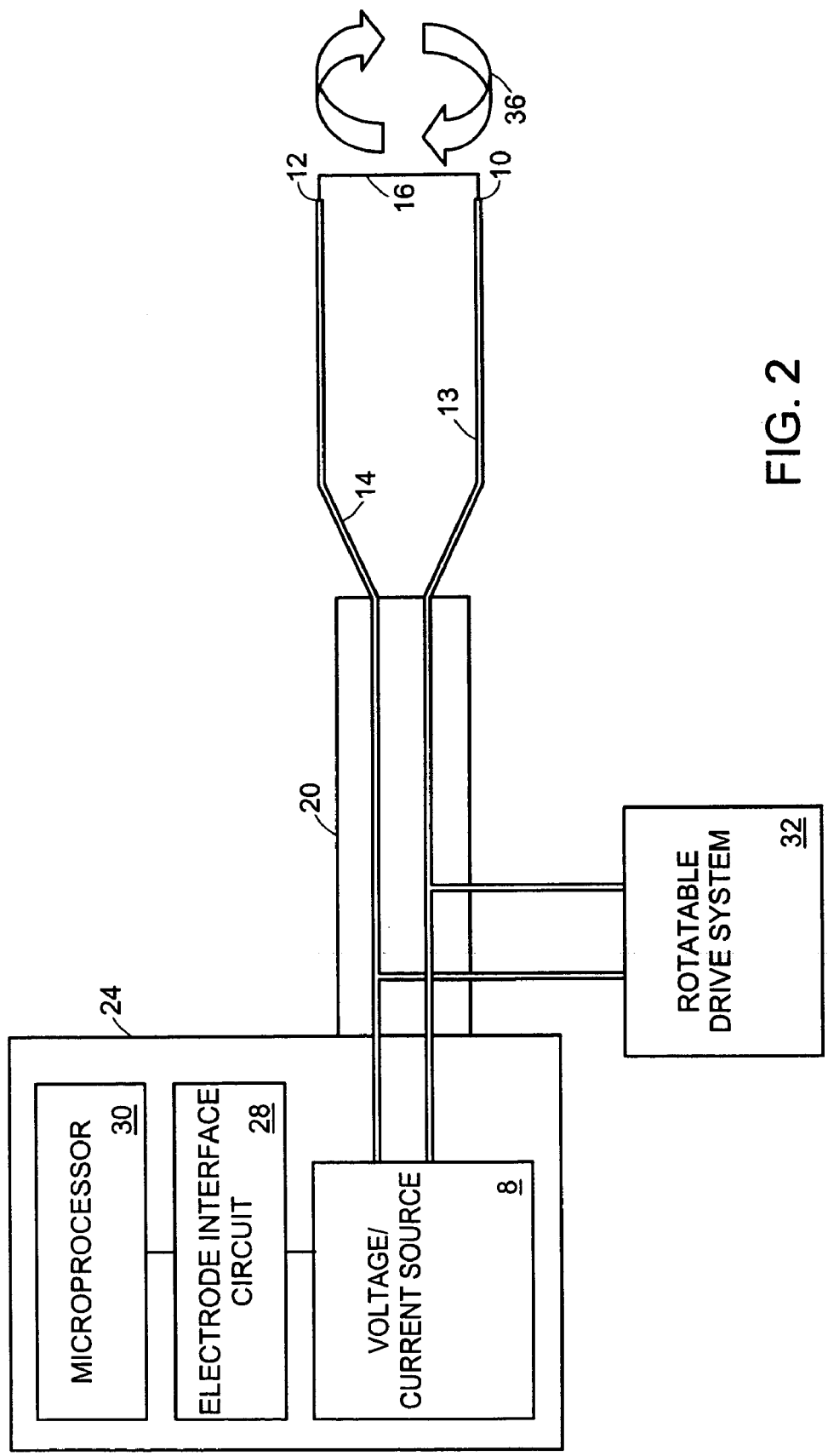
FIG. 2 shows a more detailed schematic view of the morcellator of FIG. 1A, including a rotatable RH electrode.

Referring to FIG. 1A, a morcellator 5 according to the invention is connectable to a source of electrical current 8 (which could instead be a source of voltage and which is referred to hereinafter generally as a voltage/current source or just a source), a pair of electrode leads 13, 14 and a resistance heated (RH) electrode 16 electrically coupled to proximal ends 10, 12 of the pair of electrode leads 13, 14. The pair of electrode leads 13, 14 are conductive leads made of one or more materials with relatively low electrical resistance as compared to the RH electrode 16 and, in one embodiment, are covered with an electrically insulative coating such as silicone and polyurethane. When the voltage/current source 8 is coupled to the leads 13, 14, an electrical circuit is formed from the source 8, through the electrode lead 13, through the RH electrode 16, through the other electrode lead 14, and back to the source 8. Since the resistance of the RH electrode 16 is higher than that of the pair of electrode leads 13, 14, heat is generated at the RH electrode 16 when current passes through the RH electrode 16. Heat generated at the RH electrode 16 can achieve a temperature sufficient to resect and/or comminute tissue.

Examples of suitable materials for forming the pair of electrode leads 13, 14 include, but are not limited to, copper, aluminum, silver, and combinations of two or more of such materials. Examples of suitable materials for forming the RH electrode 16 include, but are not limited to, foundry metals such as tungsten and tungsten alloys, and combinations of two or more of such materials. In another embodiment, the RH electrode 16 is made from silicon carbide. In one embodiment, the RH electrode 16 is coated with a ceramic coating.

The size and shape of the RH electrode 16 is a function of the performance needed. An RH electrode 16 having a larger cross sectional area will require higher current flow through the electrode 16 to obtain or maintain the desired heat temperature. A smaller cross sectional area may be desired for the electrode 16. The cross sectional area of the electrode leads 13, 14 also affects heat generation. A lead having a smaller cross section has a higher resistance than a lead having a larger cross section made of the same material. When resistance of the lead is high, heat can be generated in non-critical, less desirable locations reducing the effects of the electrode 16. Therefore, a larger cross section area may be desired for the electrode leads 13, 14.

In one embodiment, the RH electrode 16 is a substantially U-shaped wire loop. In another embodiment, the RH electrode 16 is a substantially U-shaped ribbon-like structure having a broad surface. Alternatively, the RH electrode 16 is formed from multiple strands of wire that are joined (e.g., soldered) together to form a loop. Although described below as a U-shaped wire loop, the RH electrode 16 can also have other configurations, such as a circular configuration.

The electrode leads 13, 14 can be any conductive path to the RH electrode 16. In one embodiment, the cross section of each electrode lead 13, 14, as taken along lines BB and CC of FIG. 1A and as shown in FIGS. 1B and 1C, is semi-circular. The electrode leads 13, 14 are also separated by an insulator 18 (as shown in FIG. 1D, which is a cross sectional view of the morcellator of FIG. 1A taken along line DD) to prevent a short circuit from occurring between the two electrode leads 13, 14. The insulator 18 can be made from any insulating material, such as rubber.

The semi-circular cross section of the electrode leads 13, 14 enables encapsulation of the electrode leads 13, 14 into an elongated inner sheath 20, whose cross section is shown in FIG. 1D. The elongated inner sheath 20 can be used as a protective measure for the electrode leads 13, 14 and may be made from fluoropolymer resins such as polytetrafluoroethylene (PTFE) and fluorinated ethylene propylene (FEP). In one embodiment, the elongated inner sheath 20 is heat shrink tubing such as teflon shrink wrap. The semi-circular cross sectional area of the electrode leads 13, 14 can maximize the cross sectional area of the electrode leads 13, 14 positioned within the lumen defined by the elongated inner sheath 20.

The RH electrode 16 can be connected to the proximal ends 10, 12 of the pair of electrode leads 13, 14 in any one of a number of ways. Examples of suitable connection methods include, but are not limited to, soldering, welding, brazing, crimping, swaging, and screwing. The connection method selected is dependent on the material of the RH electrode 16 and the electrode leads 13, 14. An important factor, however, is that no matter which connection method is employed, the connection must result in a low electrical resistance joint.

In a disclosed embodiment, the electrical voltage/current source 8 applies a relatively high direct current (DC) and a relatively low voltage to the RH electrode 16 to heat the RH electrode 16. In particular, in one embodiment, the voltage/current source 8 provides a voltage to the RH electrode 16 substantially between the range of thirty volts to sixty volts, inclusive. Additionally, in one embodiment, the voltage/current source 8 provides a current to the RH electrode 16 substantially between the range of one amp to four amps, inclusive. The voltage/current source 8 can be implemented using either linear or switching regulator technology. In either case, the output of the voltage/current source 8 must be ohmically isolated from earth ground to meet surgical instrument electrical safety standards.

Referring to FIG. 2, a morcellator controller 24 for use with the morcellator 5 includes an electrode interface circuit 28, the voltage/current source 8, and a microprocessor 30. The morcellator controller 24 measures the resistance of the RH electrode 16. The resistance of the RH electrode 16 changes as heat is withdrawn from the electrode 16 by various thermal masses including tissue, irrigants (also referred to below as irrigation fluid), and surrounding fluids. The morcellator controller 24 adjusts the current applied to the RH electrode 16 to maintain a predetermined resistance at the RH electrode 16. In some embodiments, the electrode interface circuit 28 provides information about the voltage drop across and current flow through the RH electrode 16 to the microprocessor 30. The electrode interface circuit 28 can include commercially available differential and operational amplifiers, such as those from RadioShack Corporation of Fort Worth, Tex.

The microprocessor 30 receives input (by way of, for example, a user interface) such as power settings and cut/coagulation control. The microprocessor 30 also receives input from the electrode interface 28. The microprocessor 30 converts analog signals of the voltage and current measurements of the RH electrode 16 to digital signals. The microprocessor 30 controls the heating of the RH electrode 16 according to the following exemplary algorithm. When the surgeon calls for a cutting or a coagulation procedure, for example by stepping on a foot control, the resistance of the RH electrode 16 is measured. To measure the resistance, the voltage/current source 8 energizes the RH electrode 16 with a small, known current. A voltage drop across the RH electrode 16 is measured, and the RH electrode resistance when the RH electrode 16 is positioned at the body temperature is determined using Ohm's law. This preliminary measurement of the RH electrode resistance is used to calibrate automatically the RH electrode 16, such that the RH electrode 16 can be manufactured with less stringent resistance tolerance. For example, the microprocessor 30 can use stored information (such as data stored in ROM and/or RAM and/or other data storage devices or mediums) about the temperature and resistance relationship of the RH electrode material to generate a resistance to temperature conversion formula. This formula can then be used by the microprocessor 30 to determine the temperature of the RH electrode 16 during heating of the RH electrode 16. This formula also can provide the current level necessary to achieve a desired temperature at the RH electrode 16.

During a cutting or coagulation procedure, the microprocessor 30 reads the power setting (as set, for example, by a user at an interface such as a control panel) and commands the voltage/current source 8 to heat the RH electrode 16. The power applied for heating the RH electrode 16 is controlled using an algorithm stored in and/or executed by the microprocessor 30 to achieve an effective cutting/coagulation temperature in the face of widely varying thermal loads and losses due to variations in electrode position, saline or irrigant flow, and tissue characteristics.

In one embodiment, the morcellator controller 24 is a single piece of equipment comprising the voltage/current source 8, the electrode interface 28, and the microprocessor 30. In another embodiment, the voltage/current source 8, the electrode interface 28, and the microprocessor 30 comprise separate pieces of equipment that communicate with each other.

The elongated inner sheath 20 encapsulates the pair of leads 13, 14, as shown in FIG. 2. In a further embodiment, each lead 13, 14 is further protected by an individual insulative wrapping, such as teflon shrink wrap.

In one embodiment, the morcellator 5 also includes a rotatable drive system 32 coupled to the electrode leads 13, 14. The rotatable drive system 32 imparts rotary movement to the electrode leads 13, 14 and consequently to the RH electrode 16, as shown by arrow 36. The rotation simultaneously occurs with the heating of the RH electrode 16, thereby facilitating efficient reduction in the size of the tissue segments resected (e.g., by the holmium laser). For example, the RH electrode 16 can be rotated by the rotatable drive system 32 between 13,000 revolutions per minute (RPMs) and fifty thousand RPMs while simultaneously being heated by the electrical current supplied by the voltage/current source 8.

Figure 3A:
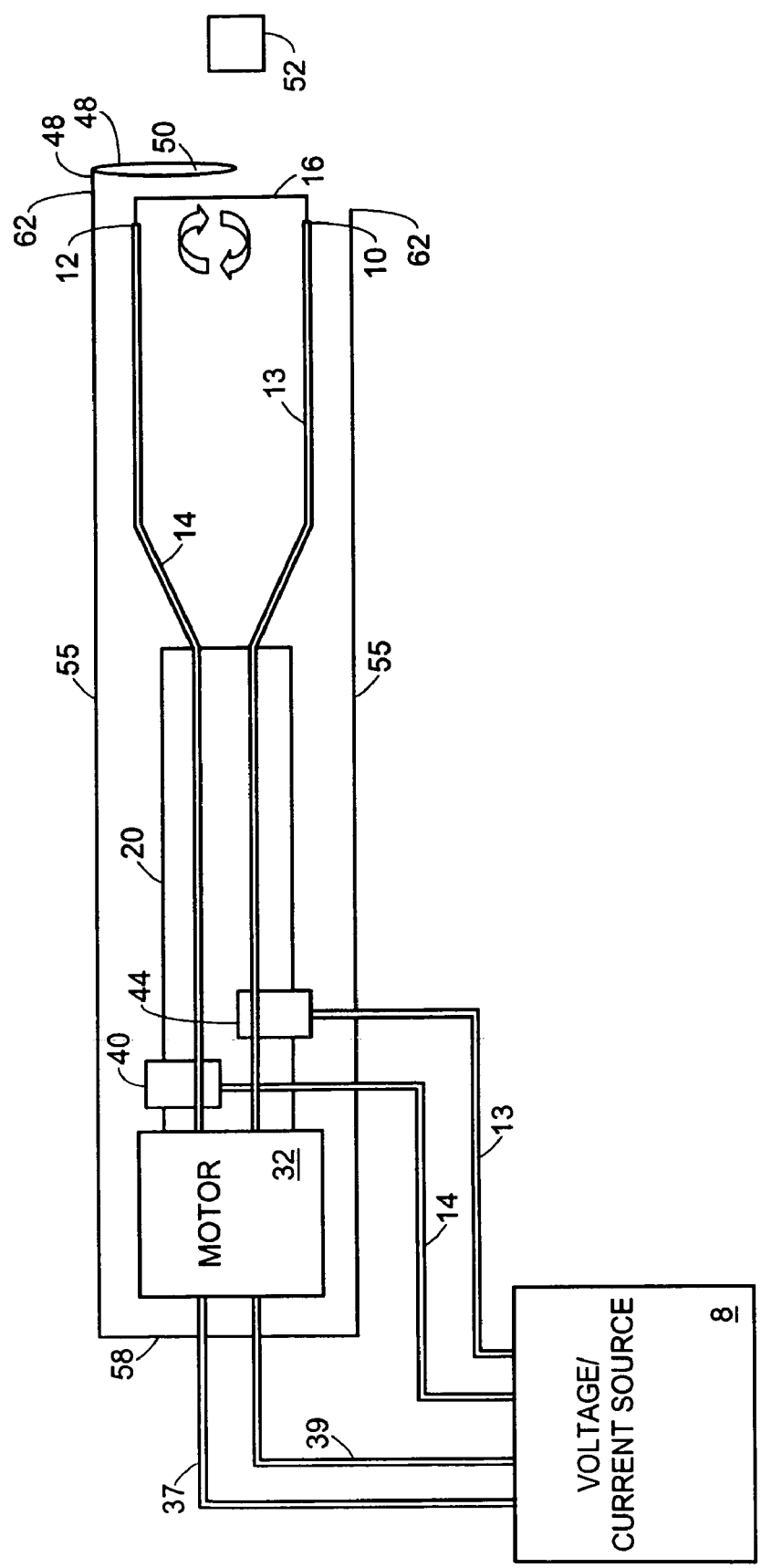
FIG. 3A is a more detailed schematic view of the morcellator of FIG. 2, including a tissue guider.

Referring to FIG. 3A, in one embodiment the rotatable drive system 32 is a DC motor that is powered by the voltage/current source 8. The motor 32 is connected to the voltage/current source 8 via a pair of motor power leads 37, 39 (i.e., a positive lead and a negative lead). To impart rotary movement on the RH electrode 16 while the voltage/current source 8 simultaneously heats the RH electrode 16, the motor 32 includes commutator rings 40, 44. The commutator rings 40, 44 couple the electrode leads 13, 14 to the motor 32 and the voltage/current source 8 and thus enable conductance of the electrical current during rotation. In one embodiment, the commutator rings 40, 44 are made up of copper segments.

Further, the morcellator 5 can include a grip activated switch that controls the rotational speed of the motor 32 proportionally to the force applied to the switch. In yet another embodiment, the rotatable drive system 32 is powered by batteries that may, for example, be located in a handle (for example, control handle 112 of FIG. 6A) of the morcellator 5.

Figure 3B:
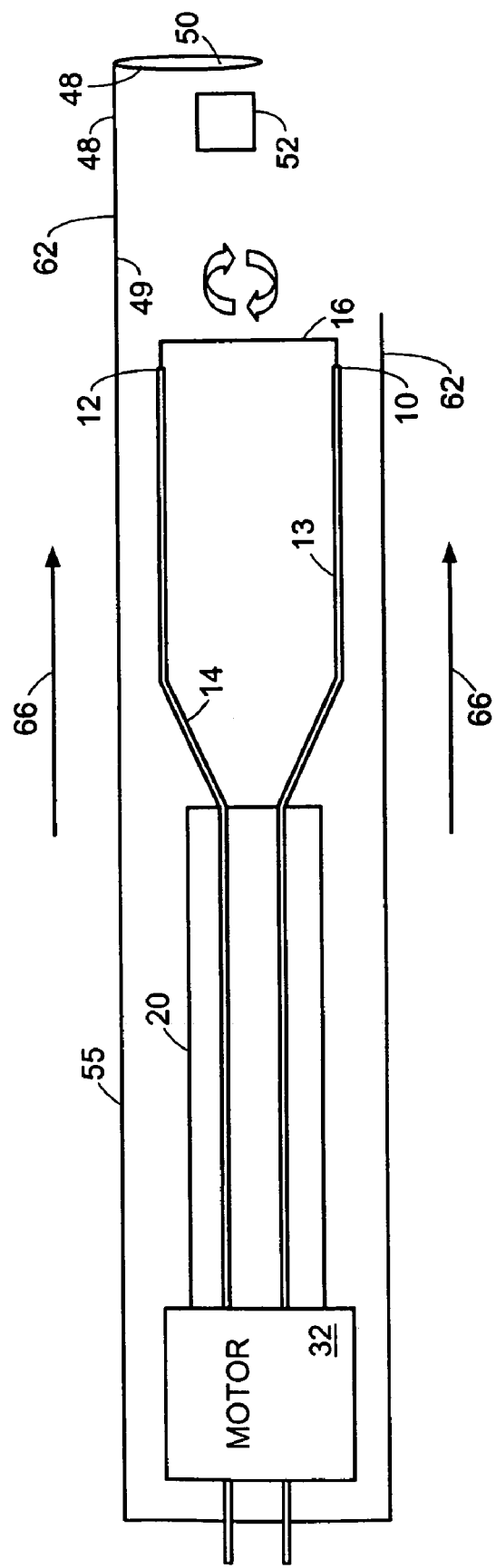
FIG. 3B is a schematic view of the morcellator of FIG. 3A in which the tissue guider is extended beyond a piece of tissue.

In one embodiment, the morcellator 5 also includes a tissue guider 48. The tissue guider 48 is used to direct a tissue segment 52, or piece, to the RH electrode 16 for morcellation. In one embodiment, the tissue segment 52 is a resected piece of tissue. However, the tissue segment 52 may also be a non-resected piece of tissue, such as a blood clot. In one embodiment, and as shown more clearly in FIG. 3B, the tissue guider 48 includes a single wire having a straight portion 49 and whose proximal end is formed into a loop 50, or elliptical ring. The loop 50 can be any size needed to be able to direct the appropriate tissue into the RH electrode 16. Furthermore, the center of the loop 50 may be off-centered relative to the center of the RH electrode 16. Although described in one embodiment as a single wire with a loop, the tissue guider 48 may be any configuration that directs the tissue segment 52 to the RH electrode 16. The tissue guider 48 directs the tissue segment 52 by, for example, pulling the tissue segment 52, pushing the tissue segment 52, or otherwise exerting a force on the tissue segment 52 (such as by blowing air onto the proximal end of the tissue segment 52 to direct it to the RH electrode 16 or by providing a suction force on the tissue segment 52 to pull it into the rotating electrode 16).

The straight portion 49 of the tissue guider 48 extends longitudinally into and out of the proximal end of an elongated outer sheath 55. The outer sheath 55 is exterior to the inner sheath 20. In one embodiment, the outer sheath 55 is a tubular member that can be made from a solid material, such as plastic, and may also be flexible to facilitate insertion into the urethra of the patient. Some or all of the straight portion 49 of the tissue guider 48 is disposed inside the outer sheath 55. In one embodiment, the outer sheath 55 has enough rigidity and strength to enable the tissue guider 48 to be disposed inside the outer sheath 55 without substantially deforming the outer sheath 55. The outer sheath 55 can additionally protect the internal components of the morcellator 5, such as the motor 32 and the RH electrode 16, by covering these components.

The tissue guider 48 can be constructed from a variety of materials, such as stainless steel wire, and can be positioned in any configuration as long as the tissue guider 48 can advance, retract, and direct the tissue segment 52 into the RH electrode 16. As shown in FIGS. 3A, 3B, 3C, 3D, and 3F, the tissue guider 48 extends from the proximal end 62 of the outer sheath 55. The extension is shown with arrow 66 in FIG. 3B and enables the tissue guider 48 to guide a tissue segment 52.

Figure 3C:
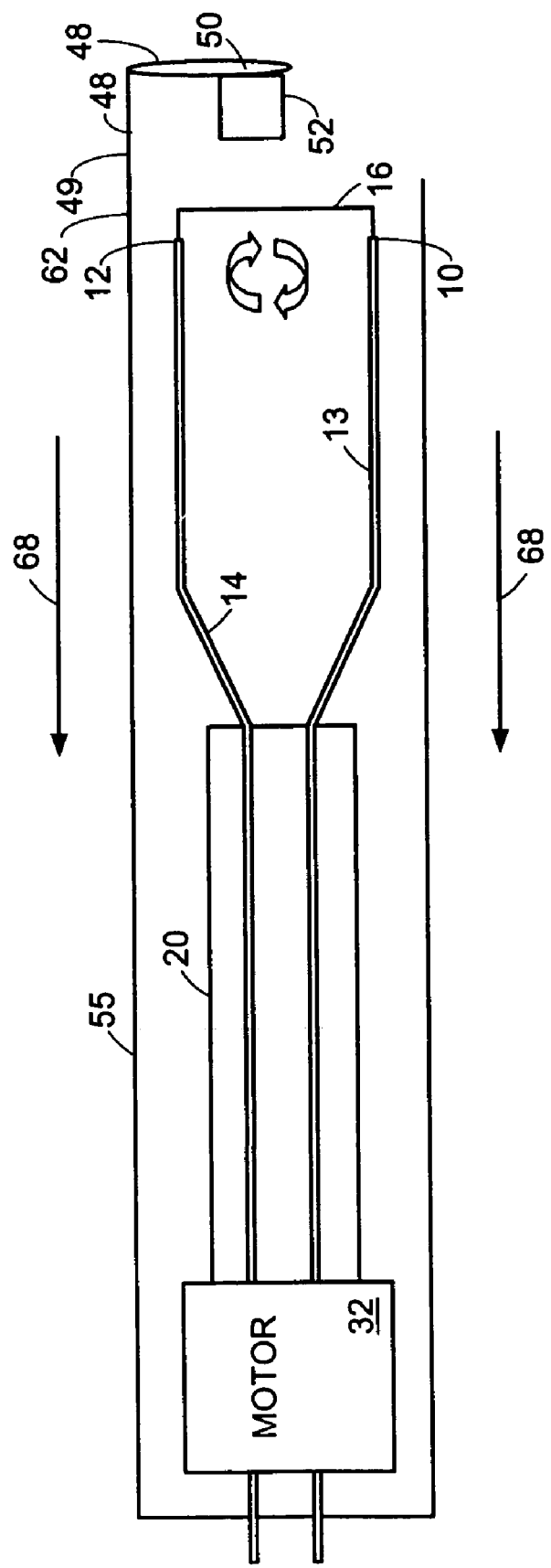
FIG. 3C is a schematic view of the morcellator of FIG. 3A in which the tissue guider is retracted to direct the piece of tissue into the rotating RH electrode.
Figure 3D:
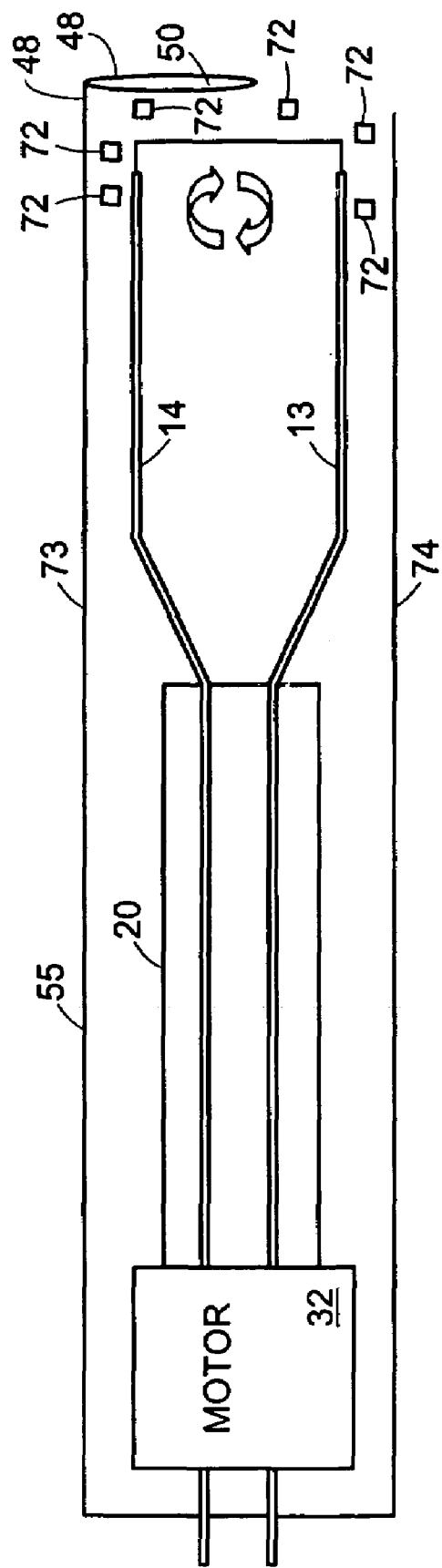
FIG. 3D is a schematic view of the morcellator of FIG. 3A in which the tissue segment has been morcellated or comminuted into smaller pieces.

Once the loop 50 of the tissue guider 48 is positioned behind the tissue segment to be morcellated and the RH electrode 16, the tissue guider 48 retracts (or, more precisely, in one embodiment, the straight portion 49 slides back into a channel or lumen in the wall of the outer sheath 55), as shown by arrow 68 in FIG. 3C, and directs the tissue segment 52 to the spinning RH electrode 16. In particular, the tissue guider 48 pushes the tissue segment 52 to the RH electrode 16. Referring to FIG. 3D, the loop 50 stops pushing the tissue segment 52 to the RH electrode 16 when the straight portion 49 is fully retracted. In one embodiment, the tissue segment 52 makes contact with the RH electrode 16 due to the momentum of the loop 50 towards the RH electrode 16 as a result of the retraction. In another embodiment, the morcellator 5 provides a suction force into the morcellator 5 to pull the tissue segment 52 into the RH electrode 16 once the tissue segment 52 comes within a particular distance of the RH electrode 16. The loop 50 can be positioned to be within the particular distance when the tissue guider 48 is fully retracted. Upon contact with the RH electrode 16, the tissue segment 52 is then comminuted into smaller tissue pieces 72.

Although the tissue guider 48 is illustrated as being slidable into and out of an upper portion 73 of the outer sheath 55, the tissue guider 48 can also be slidable into and out of a lower portion 74 of the outer sheath 55. Moreover, in another embodiment, the morcellator 5 includes two tissue guiders 48, one slidable into and out of the upper portion 73 and the other slidable into and out of the lower portion 74. Further, the size of the loop 50 of one of the tissue guiders 48 could be different than the size of the loop 50 of the other tissue guider 48.

Figure 3E:
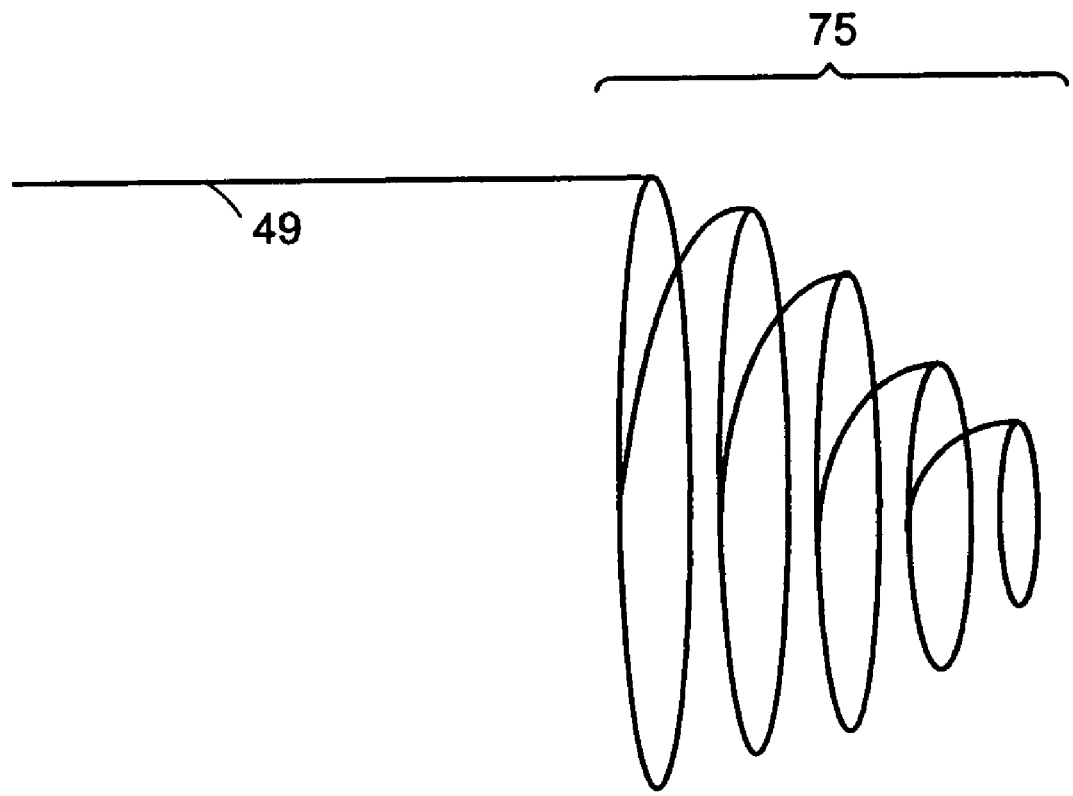
FIG. 3E is a perspective view of another embodiment of a tissue guider.

Additionally, although illustrated as elliptical, the loop 50 can be any shape, such as, but not limited to, circular, square, octagonal, triangular, and a figure eight. Also, the tissue guider 48 may include multiple loops 75 as shown in FIG. 3E. Each of the multiple loops 75 can be the same size, or each can be a different size, or some can be the same and others different, etc. The multiple loops 75 can also diminish in size to form a cone-shaped proximal end of the tissue guider 48, which may be used to catch tissue segments of various sizes. The multiple loops 75 may or may not have spaces between them. In another embodiment, the tissue guider 48 may be made from multiple wires. Examples of connection methods of the multiple wires of the tissue guider 48 include, but are not limited to, soldering, crimping, and screwing.

Figure 3F:
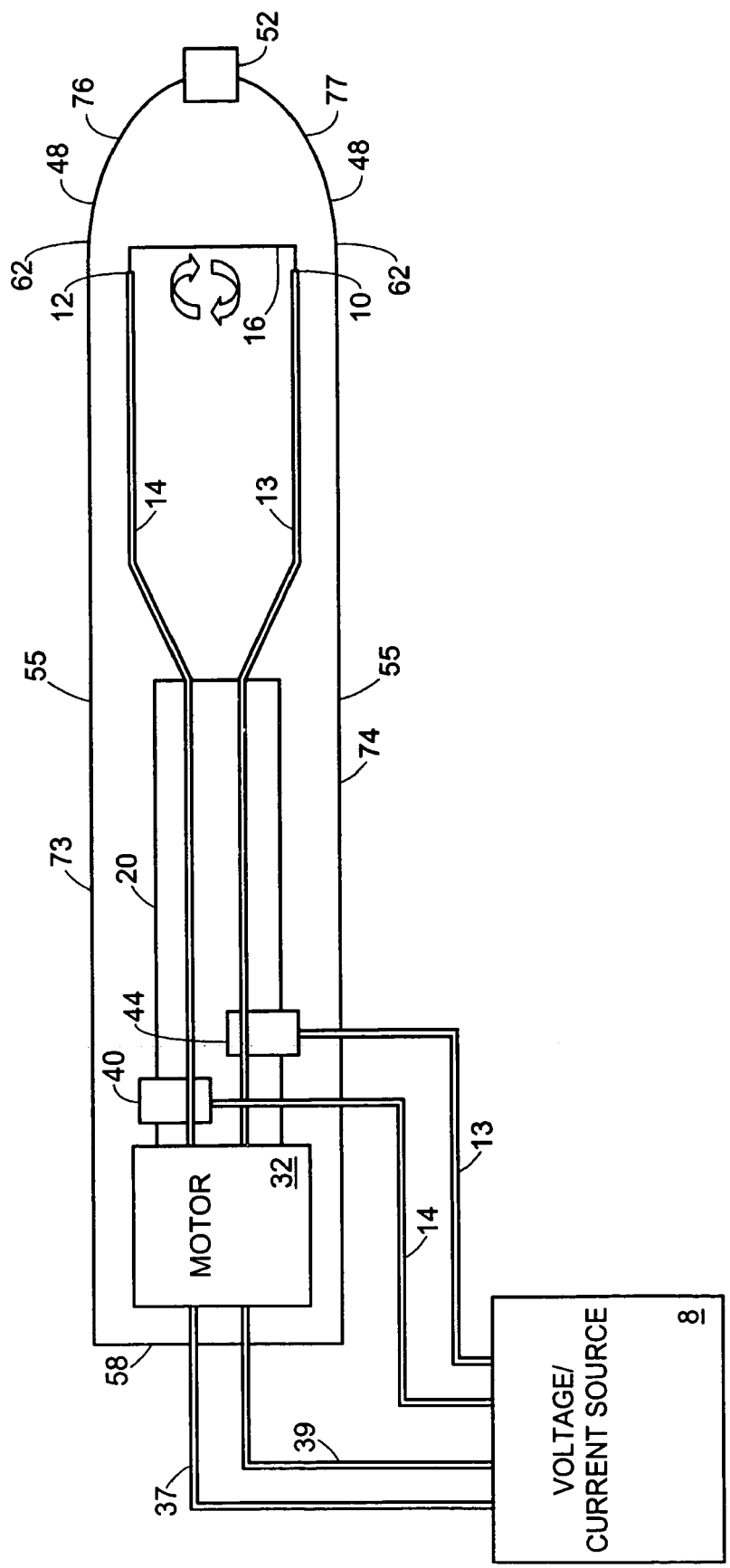
FIG. 3F illustrates a schematic view of the morcellator of FIG. 3A in which the tissue guider grasps the tissue.

Referring to FIG. 3F, another embodiment of the morcellator 5 is shown including a tissue guider 48 that grasps the tissue segment 52. In particular, the tissue guider 48 includes two wires 76, 77 that bend during extension out of the outer sheath 55 to grasp the tissue segment 52. During the retraction of the tissue guider 48, the tissue segment 52 is pulled to the RH electrode 16. Further, although the two guider wires 76, 77 begin to open as the tissue guider 48 retracts, in one embodiment the guider wires 76, 77 impart enough momentum on the tissue segment 52 to cause the tissue segment 52 to come into contact with the RH electrode 16 while the two wires 76, 77 begin to separate. Alternatively, the two guider wires 76, 77 bring the tissue segment 52 to a particular distance away from the RH electrode 16 and the morcellator 5 sucks the tissue segment 52 into the RH electrode 16 via, for instance, a suction force.

Figure 4A:
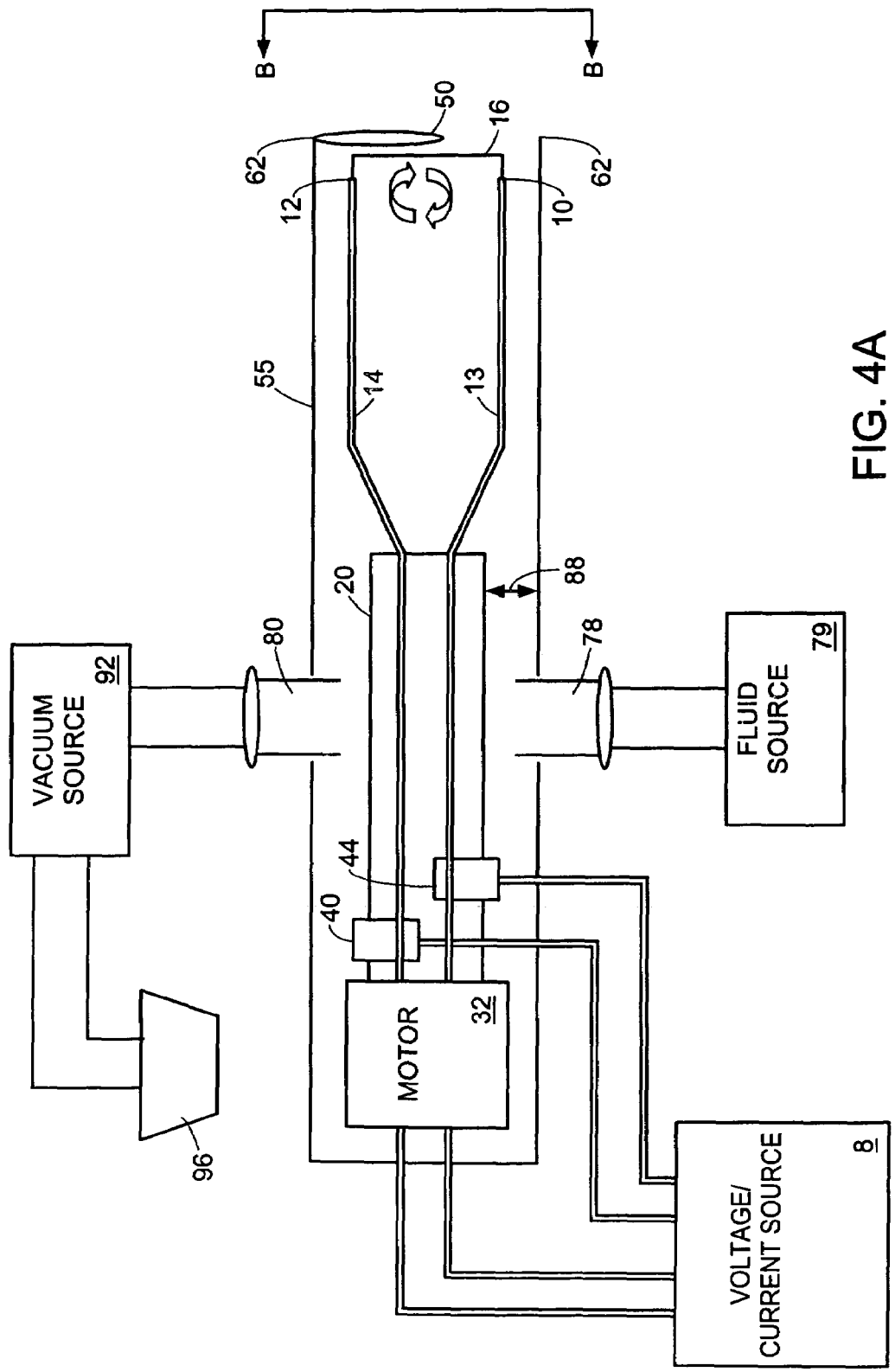
FIG. 4A is a more detailed schematic view of the morcellator of FIG. 3A, having a vacuum source and a fluid source connected to the morcellator.

To remove the morcellated tissue pieces 72 from the patient's body and/or from the morcellator 5, the morcellator 5 typically uses irrigation fluid, such as saline solution (0.9% Sodium Chloride water solution) to transport the morcellated tissue 72 out of the body and/or morcellator 5. The morcellator 5 can also use irrigation fluid to retrieve a tissue segment that has been brought to the RH electrode 16 via the tissue guider 48. In one embodiment and as shown in FIG. 4A, the morcellator 5 includes an irrigation port 78 and an aspiration port 80. The irrigation port 78 is connected to a fluid source 79 to supply the irrigation fluid to the morcellator 5. The irrigation fluid travels from the irrigation port 78 proximally towards the RH electrode 16 through an irrigation channel 88. In one embodiment, the irrigation channel 88 is defined as the distance between the outer sheath 55 and the inner sheath 20 and/or the electrode leads 13, 14.

When transporting the morcellated tissue pieces 72 out of the patient's body, the irrigation fluid comes into contact with the RH electrode 16. Additionally, the RH electrode 16 may come into contact with the patient's urine. Although contact with the urine and/or the irrigant may damage an electrode heated with radio frequency, which conducts through its outward surroundings, the contact does not damage the RH electrode 16. Rather, because the RH electrode 16 is heated using resistance heating, the contact with the irrigant and/or the urine cools the RH electrode 16. In one embodiment and as described above, the morcellator controller 24 compensates for this cooling by adjusting the current applied to the RH electrode 16 to maintain a predetermined resistance and temperature at the RH electrode 16.

The irrigation fluid, along with blood, morcellated tissue 72, and other debris, is carried away from the RH electrode 16 through the irrigation channel 88 by a vacuum source 92 connected to the aspiration port 80. In one embodiment, the vacuum source 92 is a mechanical pump capable of creating a variable vacuum and further includes a collection container 96 to collect the morcellated tissue 72 and fluids aspirated from the patient. The collection container 96 may be any size and made of any material suited to collect the irrigation fluid and other items from the morcellator 5. In one embodiment, the vacuum source 92 provides the suction force described above to bring a tissue segment 52 into contact with the RH electrode 16 if the tissue segment 52 is within a particular distance of the RH electrode 16. The medical professional operating the morcellator 5 may also actuate this suction force to morcellate the tissue segment 52.

Figure 4B:
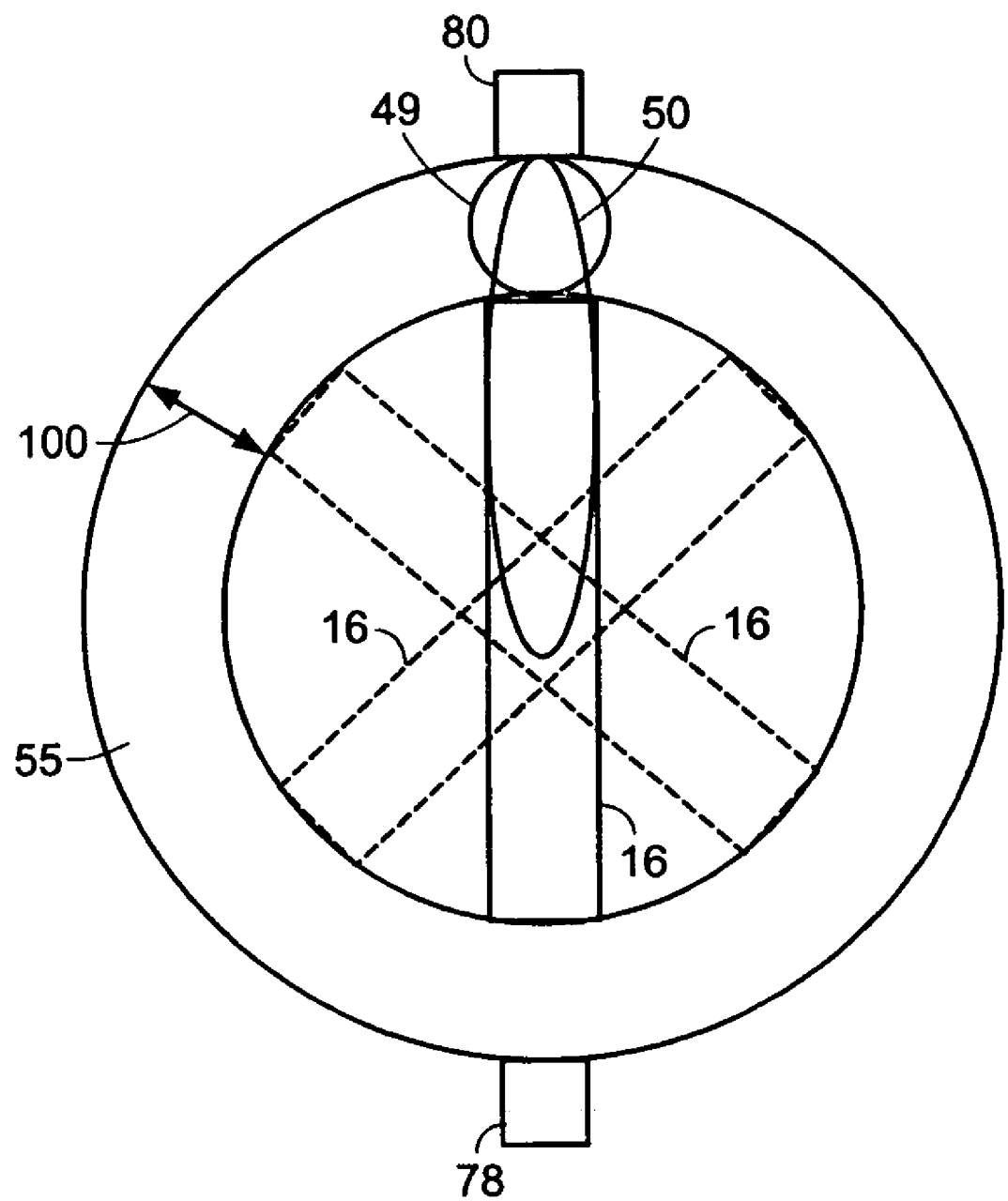
FIG. 4B is an end view of the morcellator of FIG. 4A, taken along line BB in FIG. 4A.

FIG. 4B shows an end view of the morcellator 5 of FIG. 4A, taken along line BB. The outer sheath 55 has a circular area and defines a lumen in which the RH electrode 16 rotates. In one embodiment, the single wire 49 of the tissue guider 48 has a circular cross section equivalent to the thickness 100 of the outer sheath 55. Further, the irrigation port 78 and the aspiration port 80 are located exterior to the outer sheath 55.

In one embodiment, a medical professional using the morcellator 5 searches the bladder for tissue segments 52 and then manually guides the tissue segments 52 with the tissue guider 48. For example, the medical professional activates (i.e., extends/retracts) the tissue guider 48 with a slider switch.

For example, in one embodiment the medical professional using the morcellator 5 uses an eyepiece to view the patient's body when using the morcellator 5. In one embodiment, the outer sheath 55 of the morcellator 5 passes through a resectoscope having rigid optical equipment for the viewing inside the patient's body. More specifically, the resectoscope is a 24 or 26 French (F) resectoscope. A French is a unit of distance used for measuring the diameters of tubes such as catheters and fiber optic bundles. One French is equal to ⅓ millimeter. The resectoscope can be any size (i.e., any number of French) so long as the outer sheath 55 can fit through the resectoscope. Alternatively, the insulator 18 defines a lumen and a fiber optic passes through the center of the lumen. The fiber optic terminates at the end of the insulator 18 (i.e., when the electrode leads 13, 14 separate).

In another embodiment, a tissue guider controller 104 shown in FIG. 5A actuates the tissue guider 48. In particular, the tissue guider controller 104 controls the extension and retraction of the tissue guider 48. The tissue guider controller 104 can also automate the extension and retraction of the tissue guider 48 so that the tissue guider 48 extends and retracts in a controlled and repeated fashion. In another embodiment, an operator extends the tissue guider 48 manually and the tissue guider controller 104 retracts the tissue guider 48.

Additionally, the morcellator 5 can include a sensor to help detect faults and/or failures in the morcellator 5. For example, if the tissue guider 48 does not extend or retract, a sensor could sense that the tissue guider 48 was locked in place and that a malfunction had occurred. The sensor could then alarm the medical professional of the malfunction(s). In a further embodiment, the sensor detects the rotation of the RH electrode 16 and alarms the medical professional if the motor 32 malfunctioned and was preventing the rotation of the RH electrode 16. The sensor may also detect if the voltage/current source 8 is properly heating the RH electrode 16.

Figure 5B:
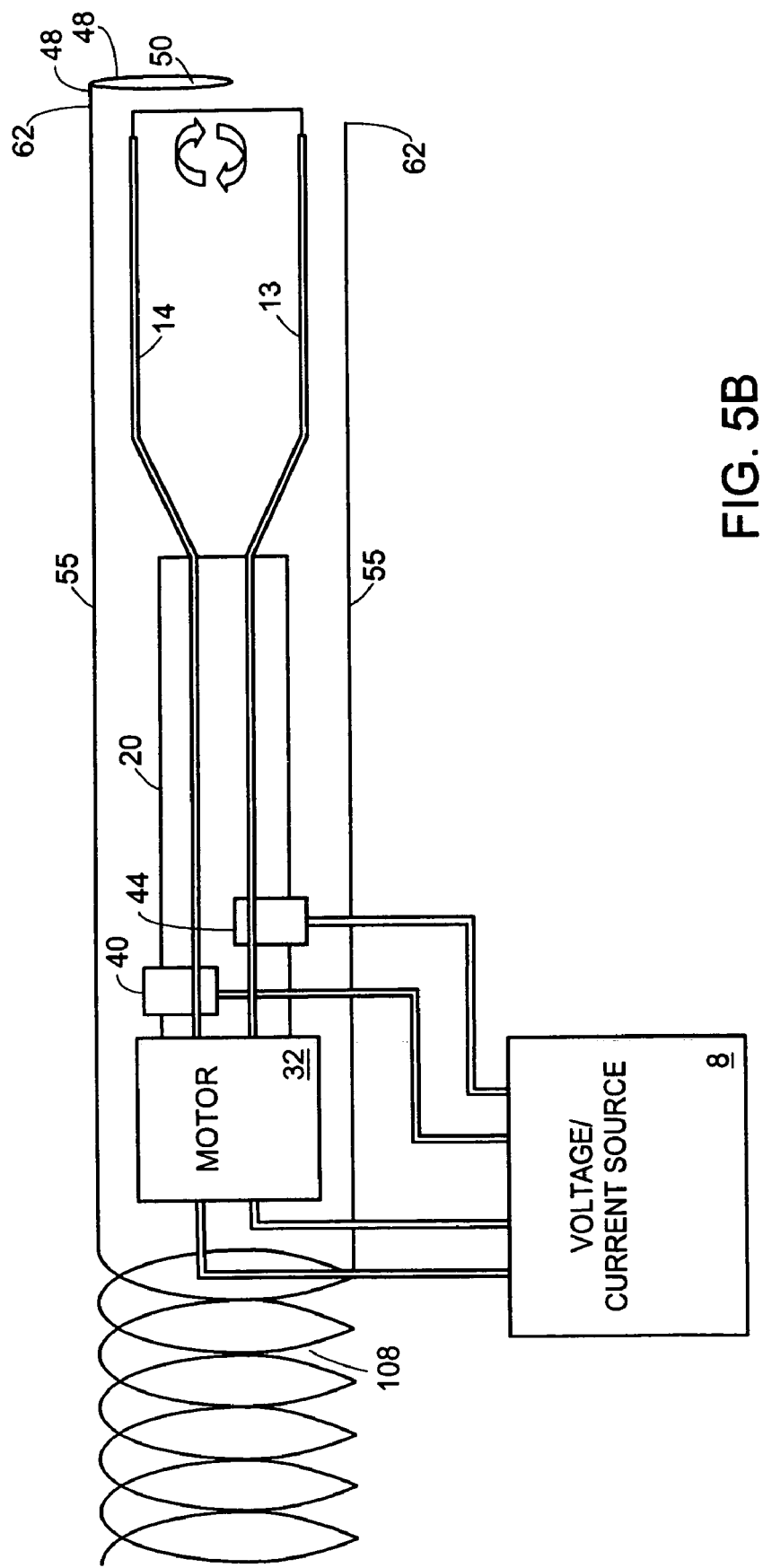
FIG. 5B illustrates a schematic view of the morcellator of FIG. 5A, including a spring.

Additionally, the tissue guider controller 104 may control the rate of retraction (i.e., the rate at which the tissue guider 48 is brought towards the morcellator 5 following extension of the tissue guider 48). For instance and as illustrated in FIG. 5B, the tissue guider controller 104 is a spring 108 having a particular spring constant. When the tissue guider 48 extends beyond the outer sheath 55, the spring 108 is extended to enable the extension of the tissue guider 48. Once the extension of the tissue guider 48 is complete, the spring 108 starts to contract back to its equilibrium state based on its spring constant. Therefore, the spring 108 enables the tissue guider 48 to retract the secured tissue segment 52 into the RH electrode 16 at a constant, or controlled, rate that is determined by the spring constant of the spring 108. The controlled retraction rate prevents too much tissue from being pulled into the RH electrode 16 at one time, which can only morcellate tissue at a certain rate that is typically dependent upon its revolutions per minute and the power applied to the RH electrode 16. Alternatively, the tissue guider controller 104 could provide a controlled retraction rate with a hydraulic or a pneumatic system.

In a further embodiment, the voltage/current source 8 is in communication with the tissue guider controller 104 to adjust the controlled rate at which the tissue guider 48 is pulled back towards the RH electrode 16. The voltage/current source 8 communicates the current and/or power applied to the RH electrode 16 and the tissue guider controller 104 adjusts the retraction rate accordingly.

Figure 6A:
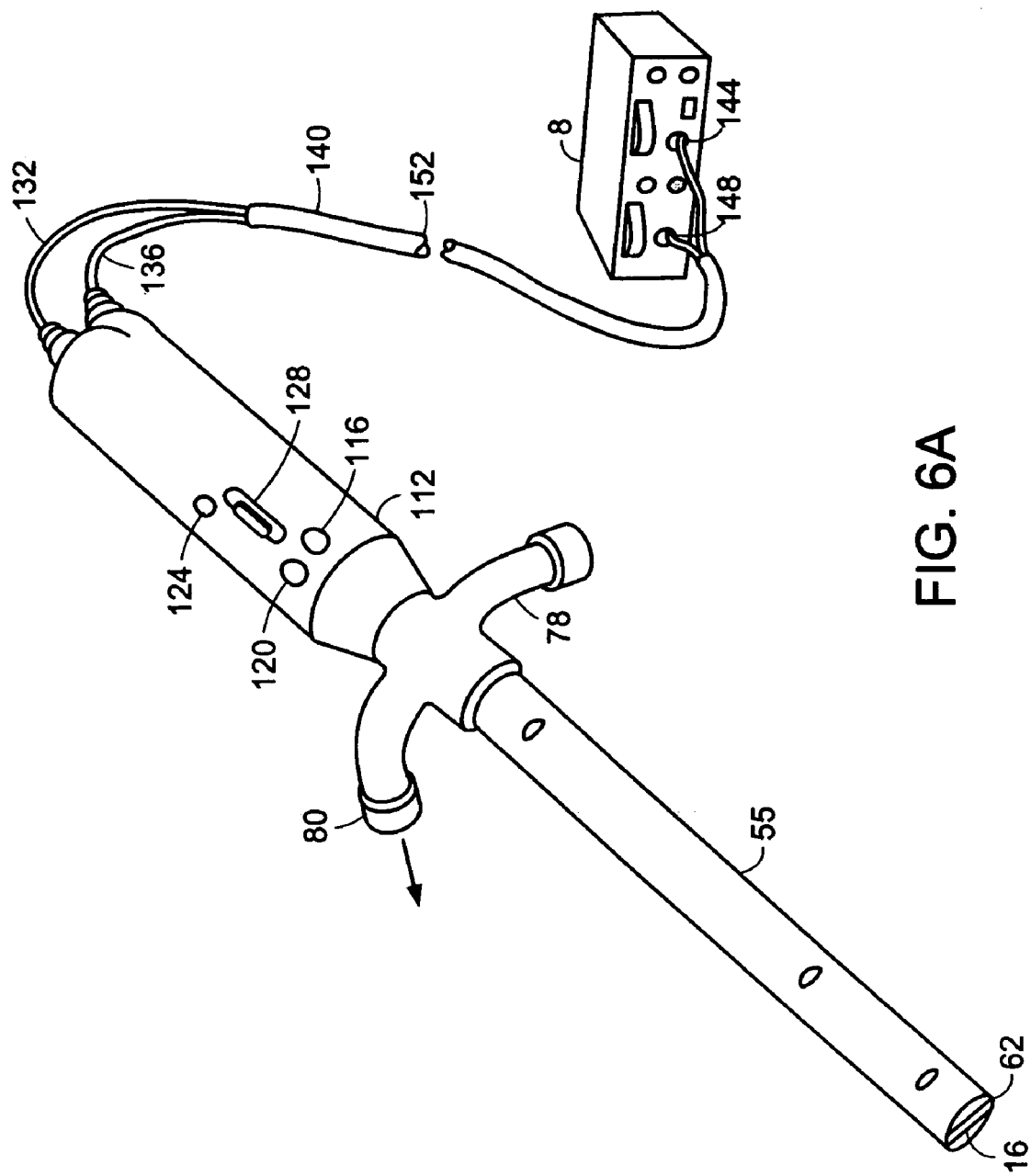
FIG. 6A shows a perspective view of an embodiment of a morcellator similar to the morcellator shown schematically in FIG. 4A.

A perspective view of one embodiment of the morcellator 5 according to the invention is shown in FIG. 6A. In one embodiment, the morcellator 5 includes a control handle 112 to operate the interrelated components of the morcellator 5. The various parameters of the morcellator components, such as rotational speed, irrigation fluid pressure, and vacuum level, as well as the actuation of the morcellator 5, may be set by actuating control knobs 116, 120, 124, and/or by sliding control switch 128. Alternatively, the actuation of the morcellator 5 and/or its components may be controlled via one or more foot pedals. Additionally, the actuation of the morcellator 5 and/or its components may be controlled via one or more foot pedals and via one or more of the control knobs 116, 120, 124 and control switch 128. For example, the operation of the morcellator 5 may be actuated by sliding control switch 128 to an "on" position, and the vacuum source 92 and fluid source 79 may be actuated by depressing a first and second foot pedal, respectively. Moreover, the control handle 112 can include any number and combination of control knobs and/or control switches.

In one embodiment, the pair of electrode leads 13, 14 are protected by and grouped into an electrode leads insulative wrapping 132 for the pair of electrode leads 13, 14. The pair of electrode leads 13, 14 are also individually insulated from each other within the electrode leads insulative wrapping 132. The motor power leads 37, 39 are additionally protected by and grouped into a motor power leads insulative wrapping 136. The pair of motor power leads 37, 39 are also individually insulated from each other within the motor power leads insulative wrapping 136.

The two insulative wrappings 132, 136 are further grouped into an outer insulative wrapping 140 to provide an uncluttered and organized connection to the voltage/current source 8. The motor power leads 37, 39 and the electrode leads 13, 14 are then separated before connecting to an electrode lead terminal 144 and a motor power lead terminal 148. In particular, one of the electrode leads 13, 14 connects to a positive electrode lead terminal and the other electrode lead 13, 14 connects to a negative electrode lead terminal of the voltage/current source 8. Likewise, one of the motor power leads 37, 39 connects to a positive motor power lead terminal and the other motor power lead 37, 39 connects to a negative motor power lead terminal. In one embodiment, the positive terminals and the negative terminals for the electrode leads 13, 14 and the motor power leads 37, 39 are independent from each other. Alternatively, the positive motor power lead 37, 39 and the positive electrode lead 13, 14 connect to the same positive terminal and the negative motor power lead 37, 39 and the negative electrode lead 13, 14 connect to the same negative terminal.

In a further embodiment, one end of the insulative wrappings 132, 136, 140 (and thus one end of each lead 13, 14, 37, 39) can be disconnected from the other end of the respective insulative wrappings 132, 136, 140 (and thus the other end of each lead 13, 14, 37, 39) at a particular disconnect location 152. This may be useful, for instance, if the voltage/current source 8 is secured to a table or workbench and an operator of the morcellator 5 has to move the rest of the morcellator 5 (e.g., the control handle 112, the elongated outer sheath 55) to another location, perhaps to repair a component of the morcellator 5. The disconnect location 152 may consist of two mating connectors that can easily be connected and disconnected by, for instance, twisting, pulling, or pushing the two mating connectors. Alternatively, actuation of a button on the control handle 112 or a foot pedal could disconnect the mating connectors.

Figure 6B:
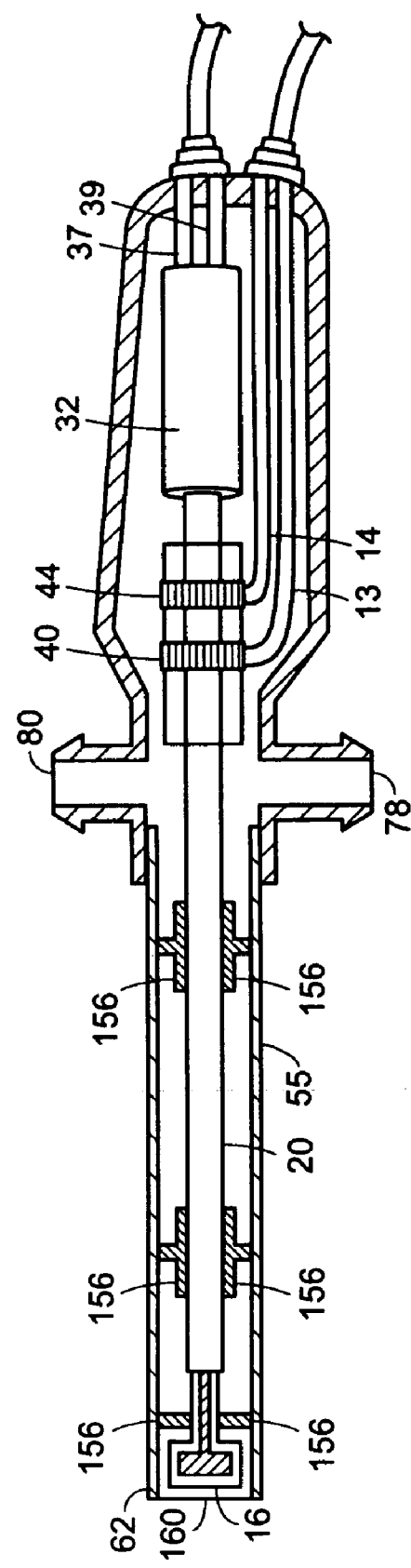
FIG. 6B shows a partial cross-sectional view of the morcellator of FIG. 6A.

FIG. 6B shows a side view of the morcellator 5 of FIG. 6A. In one embodiment, the morcellator 5 includes bearings 156 at particular locations to support the components of the morcellator (e.g., the inner sheath 20) and to reduce friction between the moving components (e.g., the inner sheath 20) of the morcellator 5. The bearings can be, for instance, ball bearings, ball thrust bearings, roller bearings, or bushings. The bearings can be made from a variety of material or combinations of materials, such as plastic, stainless steel, iron, chrome, nickel, zinc, and bronze. Additionally, when not in use, the proximal end of the RH electrode 16 may be protected by a protective covering 160.

The medical professional inserts the proximal end 62 of the morcellator 5 into the patient's body until the tissue to be morcellated is at least a particular distance away from the proximal end 62. The particular distance is a distance at which the tissue guider 48 can extend far enough out to be able to push the tissue back to the RH electrode 16. In some embodiments, the medical professional uses the eyepiece described above to determine how far to insert the morcellator 5 into the patient's body to morcellate the tissue. Typically, the entire outer elongated sheath 55 can be inserted into the patient's body until reaching the control handle 112.

Variations, modifications, and other implementations of what is described herein will occur to those of ordinary skill in the art without departing from the spirit and the scope of the invention. The invention is not to be limited only to the preceding illustrative description.

What is claimed is:

1. A morcellator, comprising:
   (a) a rotatable electrode at least partially housed in an outer sheath, having a resistance to a flow of an electrical current, and being heatable by the flow of the current through the rotatable electrode;
   (b) a drive system for rotating the rotatable electrode as the rotatable electrode is heated by the flow of the current; and
   (c) a tissue guider moveable with respect to the outer sheath for directing a tissue segment to the rotatable electrode for morcellation.

2. The morcellator of claim 1 further comprising a source of the electrical current, the source being couplable to the rotatable electrode.

3. The morcellator of claim 2 wherein the source generates a voltage of substantially greater than thirty volts and substantially less than sixty volts.

4. The morcellator of claim 2 wherein the source supplies the electrical current to the electrode so that the electrode is maintained at a temperature sufficient to comminute tissue.

5. The morcellator of claim 2 further comprising a commutator coupling the electrode, the source, and the drive system to allow simultaneous heating and rotation of the electrode.

6. The morcellator of claim 1 further comprising a vacuum source couplable to the outer sheath to provide suction.

7. The morcellator of claim 6 further comprising a catch container coupled to the vacuum source.

8. The morcellator of claim 1 wherein a proximal end of the tissue guider comprises a loop.

9. The morcellator of claim 1 wherein the drive system comprises a motor.

10. The morcellator of claim 1 further comprising a tissue guider controller coupled to the tissue guider to enable the guider to direct tissue to the rotatable electrode at a predetermined rate.

11. The morcellator of claim 10 wherein the guider controller comprises a spring.

12. The morcellator of claim 1 further comprising a fluid source couplable to the outer sheath to provide irrigation fluid.

13. The morcellator of claim 1 further comprising an electrode interface circuit coupled to the electrode to provide information about a voltage drop across and the flow of the current through the rotatable electrode.

14. A morcellator, comprising:
   (a) means for heating a rotatable electrode having a resistance to a flow of an electrical current by the flow of the current, the rotatable electrode being at least partially housed in an outer sheath;
   (b) means for rotating the rotatable electrode as the rotatable electrode is heated by the flow of the current; and
   (c) means, moveable with respect to the outer sheath, for directing a tissue segment to the rotatable electrode for morcellation.

* * * * *

UNITED STATES PATENT AND TRADEMARK OFFICE
CERTIFICATE OF CORRECTION

PATENT NO. : 6,997,926 B2
DATED : February 14, 2006
INVENTOR(S) : Barry N. Gellman et al.

It is certified that error appears in the above-identified patent and that said Letters Patent is hereby corrected as shown below:

<u>Title page,</u>
Item [75], Inventors, "Josef Slanda" should read -- Jozef Slanda --.

Signed and Sealed this

Thirtieth Day of May, 2006

JON W. DUDAS
*Director of the United States Patent and Trademark Office*